United States Patent
Hino

(10) Patent No.: US 10,820,784 B2
(45) Date of Patent: Nov. 3, 2020

(54) STEREOSCOPIC ENDOSCOPE APPARATUS AND VIDEO PROCESSOR USING TWO IMAGES FORMED BY OBJECTIVE OPTICAL SYSTEM

(71) Applicant: OLYMPUS CORPORATION, Tokyo (JP)

(72) Inventor: Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 495 days.

(21) Appl. No.: 15/796,937

(22) Filed: Oct. 30, 2017

(65) Prior Publication Data

US 2018/0042453 A1 Feb. 15, 2018

Related U.S. Application Data

(63) Continuation of application No. PCT/JP2016/061668, filed on Apr. 11, 2016.

(30) Foreign Application Priority Data

May 14, 2015 (JP) .................................. 2015-099324

(51) Int. Cl.
*A61B 1/04* (2006.01)
*G02B 23/24* (2006.01)
(Continued)

(52) U.S. Cl.
CPC ............ *A61B 1/00009* (2013.01); *A61B 1/00* (2013.01); *A61B 1/0005* (2013.01);
(Continued)

(58) Field of Classification Search
None
See application file for complete search history.

(56) References Cited

U.S. PATENT DOCUMENTS

2006/0002601 A1* 1/2006 Fu .......................... G06T 11/008
382/132
2006/0074292 A1* 4/2006 Thomson ............. A61B 6/5217
600/411
(Continued)

FOREIGN PATENT DOCUMENTS

JP H06261341 A 9/1994
JP 2003334160 A 11/2003
(Continued)

OTHER PUBLICATIONS

International Search Report dated Jun. 28, 2016 issued in PCT/JP2016/061668.
(Continued)

*Primary Examiner* — John P Leubecker
*Assistant Examiner* — Minqiao Huang
(74) *Attorney, Agent, or Firm* — Scully, Scott, Murphy & Presser, P.C.

(57) ABSTRACT

A stereoscopic endoscope apparatus includes: an image pickup device configured to pick up optical images for a right eye and a left eye; a similarity degree determination portion configured to receive input of an image signal for the right eye and an image signal for the left eye outputted from the image pickup device, and calculate a similarity degree between the image for the right eye and the image for the left eye; and an image signal output portion configured to switch and output a three-dimensional image signal formed of the image signal for the right eye and the image signal for the left eye and a two-dimensional image signal formed of either one of the image signal for the right eye and the image signal for the left eye, based on the similarity degree calculated by the similarity degree determination portion.

14 Claims, 5 Drawing Sheets

(51) Int. Cl.
*H04N 13/106* (2018.01)
*H04N 5/225* (2006.01)
*A61B 1/00* (2006.01)
*A61B 5/00* (2006.01)
*H04N 13/00* (2018.01)

(52) U.S. Cl.
CPC ............ *A61B 1/00193* (2013.01); *A61B 1/04* (2013.01); *A61B 5/748* (2013.01); *A61B 5/7485* (2013.01); *G02B 23/24* (2013.01); *G02B 23/2415* (2013.01); *H04N 13/106* (2018.05); *H04N 13/158* (2018.05); *H04N 2005/2255* (2013.01); *H04N 2013/0074* (2013.01)

(56) References Cited

U.S. PATENT DOCUMENTS

| | | | | |
|---|---|---|---|---|
| 2007/0260137 A1* | 11/2007 | Sato | ............ | G06T 5/50 600/407 |
| 2011/0115882 A1* | 5/2011 | Shahinian | ................ | A61B 1/05 348/45 |
| 2013/0033576 A1* | 2/2013 | Myokan | ............... | H04N 13/239 348/46 |
| 2014/0350338 A1* | 11/2014 | Tanaka | ............... | A61B 1/00193 600/111 |
| 2015/0002812 A1* | 1/2015 | Yoshihara | ................. | G06T 7/32 351/206 |
| 2015/0227779 A1* | 8/2015 | Kawai | ..................... | G06K 5/008 382/154 |
| 2015/0235373 A1* | 8/2015 | Kato | .................. | A61B 1/00009 348/51 |
| 2016/0259159 A1* | 9/2016 | Matsui | ................. | H04N 13/239 |
| 2017/0086649 A1* | 3/2017 | Mizuno | ................. | H04N 5/2254 |
| 2017/0303770 A1* | 10/2017 | Takahashi | ............ | A61B 1/0051 |

FOREIGN PATENT DOCUMENTS

| | | |
|---|---|---|
| JP | 2005296467 A | 10/2005 |
| JP | 2007044153 A | 2/2007 |
| JP | 2010068309 A | 3/2010 |

OTHER PUBLICATIONS

Japanese Office Action dated Jan. 10, 2017 issued in JP 2016-564117.

* cited by examiner

STEREOSCOPIC ENDOSCOPE APPARATUS AND VIDEO PROCESSOR USING TWO IMAGES FORMED BY OBJECTIVE OPTICAL SYSTEM

CROSS REFERENCE TO RELATED APPLICATION

This application is a continuation application of PCT/JP2016/061668 filed on Apr. 11, 2016 and claims benefit of Japanese Application No. 2015-099324 filed in Japan on May 14, 2015, the entire contents of which are incorporated herein by this reference.

BACKGROUND OF THE INVENTION

1. Field of the Invention

The present invention relates to a stereoscopic endoscope apparatus, and in particular relates to a stereoscopic endoscope apparatus and a video processor that switches display from a three-dimensional image to a two-dimensional image.

2. Description of the Related Art

Conventionally, an endoscope apparatus has been widely utilized in a medical field and an industrial field. An endoscope includes an elongated insertion portion, and a user can display an object image through an observation window provided on a distal end portion of the insertion portion on a monitor and observe a subject or an object.

In addition, in recent years, a stereoscopic endoscope apparatus that receives reflected light from a subject or an object through two observation windows and enables stereoscopic vision of the subject or the object has been put into practical use. According to the stereoscopic endoscope apparatus, a user can stereoscopically view a lesion for example so that it is easy to observe and treat the lesion.

In addition, Japanese Patent Application Laid-Open Publication No. 2003-334160 proposes and discloses an endoscope apparatus capable of switching a three-dimensional image of a narrow visual field for stereoscopic vision and a two-dimensional image of a wide visual field which allows observation of a peripheral portion in order to recognize a situation around a diseased site, in the stereoscopic endoscope apparatus.

Furthermore, Japanese Patent Application Laid-Open Publication No. 2005-296467 proposes and discloses an endoscope apparatus that reduces variance of left and right images and allows the stereoscopic vision without unnatural feelings in the stereoscopic endoscope apparatus.

When a foreign matter is stuck to the observation window at the distal end portion of the insertion portion while observation or treatment is being performed by the stereoscopic endoscope apparatus, a user can remove the foreign matter stuck to the observation window by operating an air/water feeding button and jetting water and air from an air/water feeding nozzle.

SUMMARY OF THE INVENTION

A stereoscopic endoscope apparatus of the present invention includes: an image pickup portion configured to pick up first and second optical images formed by an objective optical system configured to form the first and second optical images; a similarity degree calculation portion configured to receive input of a first image signal based on the first optical image and a second image signal based on the second optical image outputted from the image pickup portion, compare a first image based on the first image signal and a second image based on the second image signal, and calculate a similarity degree between the first image and the second image; and an image signal output portion configured to switch from a three-dimensional image signal formed of the first image signal and the second image signal to a two-dimensional image signal formed of either one of the first and second image signals based on an image with fewer foreign matters between the first image signal and the second image signal and output the two-dimensional image signal, when, due to sticking of the foreign matters to a portion of the objective optical system, the similarity degree becomes lower than the similarity degree when the foreign matters are not stuck.

A video processor of the present invention includes: a similarity degree calculation portion configured to receive a first image signal generated by image pickup of a first optical image formed by an objective optical system and a second image signal generated by image pickup of a second optical image formed by the objective optical system, compare a first image based on the first image signal and a second image based on the second image signal, and calculate a similarity degree between the first image and the second image; and an image signal output portion configured to switch from a three-dimensional image signal formed of the first image signal and the second image signal to a two-dimensional image signal formed of either one of the first and second image signals based on an image with fewer foreign matters between the first image signal and the second image signal and output the two-dimensional image signal, when, due to sticking of the foreign matters to a portion of the objective optical system, the similarity degree becomes lower than the similarity degree when the foreign matters are not stuck.

DETAILED DESCRIPTION OF THE PREFERRED EMBODIMENT(S)

Hereinafter, an embodiment of the present invention will be described with reference to the drawings.
(Configuration)

Figure 1:
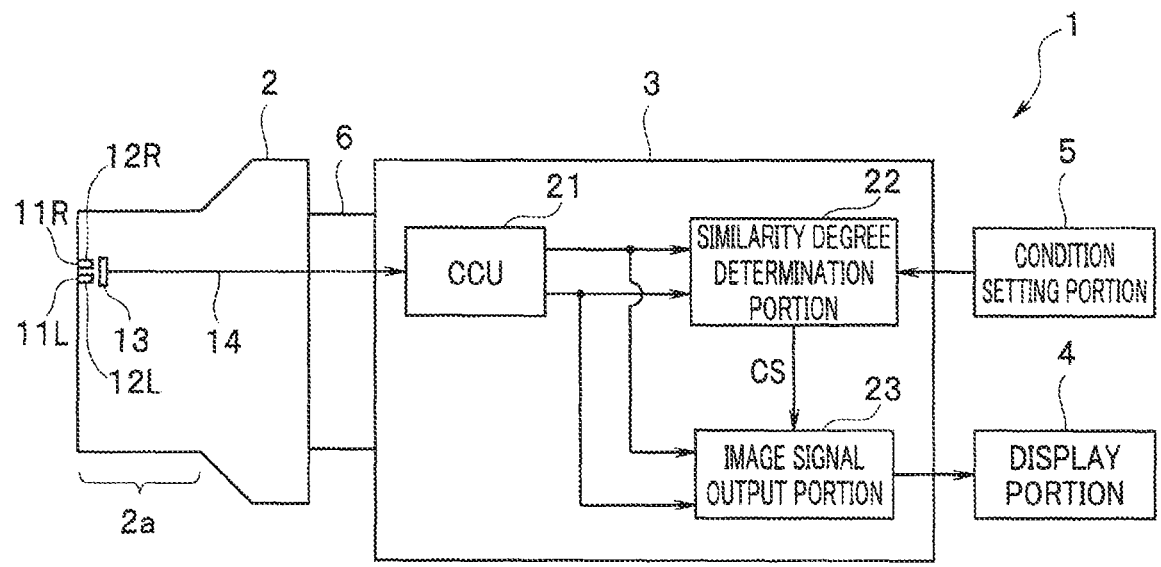
FIG. 1 is a configuration diagram illustrating a configuration of a stereoscopic endoscope apparatus relating to an embodiment of the present invention.

FIG. 1 is a configuration diagram illustrating a configuration of a stereoscopic endoscope apparatus relating to the present embodiment.

A stereoscopic endoscope apparatus 1 is configured including an endoscope 2, a video processor 3, a display portion 4, and a condition setting portion 5. The endoscope 2 and the video processor 3 are connected through a cable 6.

The endoscope 2 is a stereoscopic endoscope that picks up a stereoscopic image. The endoscope 2 includes an elongated insertion portion 2a, and includes two observation windows 11R and 11L on which reflected light from an observation target is made incident at a distal end portion of the insertion portion 2a. On a rear side of the two observation windows 11R and 11L, objective optical systems 12R and 12L are disposed respectively. The endoscope 2 includes an image pickup device 13 such as a CCD, disposed at a focus position of the objective optical systems 12R and 12L. The image pickup device 13 is connected with the video processor 3 by a signal line 14 inserted to the cable 6.

The observation window 11R is an observation window for a right eye for stereoscopic vision, and the observation window 11L is an observation window for a left eye for the stereoscopic vision. Light made incident on the respective observation windows 11R and 11L passes through the corresponding objective optical systems 12R and 12L, and forms an image on an image pickup surface of the image pickup device 13.

The image pickup device 13 photoelectrically converts an optical image formed on the image pickup surface, and outputs an image pickup signal to the signal line 14. The outputted image pickup signal is an image signal of a rectangular image pickup surface. The image pickup signal outputted from the image pickup device 13 includes an image for the right eye and an image for the left eye.

That is, the image pickup device 13 configures an image pickup portion configured to pick up two optical images formed by the objective optical systems that form the two optical images. More specifically, the image pickup device 13 which is the image pickup portion picks up the optical image for the right eye formed by the objective optical system 12R that forms the optical image for the right eye and the optical image for the left eye formed by the objective optical system 12L that forms the optical image for the left eye.

The video processor 3 includes a camera control unit (referred to as a CCU, hereinafter) 21, a similarity degree determination portion 22, and an image signal output portion 23.

The CCU 21 is an image signal generation circuit configured to receive the image pickup signal from the image pickup device 13, and generate the image for the right eye and the image for the left eye included in the image pickup signal.

The two image signals of the image for the right eye and the image for the left eye generated in the CCU 21 are outputted to the similarity degree determination portion 22 and the image signal output portion 23.

The similarity degree determination portion 22 includes circuits such as a central processing unit (CPU), a ROM and a RAM, and performs processing of calculating a similarity degree between the two images based on the two image signals of the image for the right eye and the image for the left eye from the CCU 21, and outputting a determination signal CS determined by comparing the calculated similarity degree with a predetermined threshold. A calculation method of the similarity degree will be described later.

That is, the similarity degree determination portion 22 configures a similarity degree calculation portion configured to receive input of a first image signal based on a first optical image and a second image signal based on a second optical image outputted from the image pickup device 13, compare a first image based on the first image signal and a second image based on the second image signal, and calculate the similarity degree between the first image and the second image. More specifically, the similarity degree determination portion 22 configures the similarity degree calculation portion configured to compare the image for the right eye and the image for the left eye and calculate the similarity degree between the image for the right eye and the image for the left eye by receiving the input of the image signal for the right eye based on the optical image for the right eye and the image signal for the left eye based on the optical image for the left eye outputted from the image pickup device 13.

The image signal output portion 23 receives the two image signals of the image for the right eye and the image for the left eye from the CCU 21, and outputs the two left and right image signals for three-dimensional image display or either left or right image signal for two-dimensional image display to the display portion 4, based on the determination signal CS from the similarity degree determination portion 22.

Specifically, the image signal output portion 23 outputs only one of the two image signals of the image for the right eye and the image for the left eye to the display portion 4, when receiving a control signal CS2 which is the determination signal CS to output a two-dimensional image while the three-dimensional image display for the stereoscopic vision is instructed. In addition, the image signal output portion 23 outputs the two image signals of the image for the right eye and the image for the left eye to the display portion 4 when receiving a control signal CS3 which is the determination signal CS to output a three-dimensional image.

That is, the image signal output portion 23 switches and outputs a three-dimensional image signal formed of the two image signals and a two-dimensional image signal formed of either one of the two image signals, based on the calculated similarity degree.

Note that, here, the image signal output portion 23 outputs the two image signals of the image for the right eye and the image for the left eye to the display portion 4 when receiving the control signal CS3; however, the similarity degree determination portion 22 may calculate the similarity degree and output only the control signal CS2 when the similarity degree satisfies a predetermined condition and the image signal output portion 23 may output only one of the two image signals of the image for the right eye and the image for the left eye to the display portion 4 when receiving the control signal CS2 and output the two image signals of the image for the right eye and the image for the left eye to the display portion 4 when not receiving the control signal CS2.

The display portion 4 is a monitor such as a liquid crystal display device. At the display portion 4, the left and right images are alternately displayed. A user can stereoscopically view an object image by utilizing spectacles for the stereoscopic vision for the left and right images displayed at the display portion 4 for example and looking at the display portion 4.

The condition setting portion 5 is an input device for inputting and setting various kinds of conditions to the similarity degree determination portion 22. The various kinds of conditions are, here, a position and a size of a region of a template image to be described later, a threshold TH to be described later, and a period PD to be described later, and an operator who is a user can arbitrarily set and change the various kinds of conditions from the condition setting portion 5. Therefore, the condition setting portion 5 is a setting portion for changing setting regarding a predetermined threshold for the similarity degree determination portion 22, and the period PD and the threshold TH can be set and changed.

The condition setting portion 5 is, for example, a keyboard or a personal computer connected to the video processor 3, or an operation panel of the video processor 3.

Therefore, the user may set a desired region of a center part for example in a main image MI to be described later as a template image TI to be described later, set the threshold TH at a desired value and also set the period PD at a desired value.

Note that the video processor 3 also includes the operation panel (not illustrated) and a control portion (not illustrated) configured to execute processing according to operation input of the user to the operation panel, or the like.

(Action)

The stereoscopic endoscope apparatus 1 is capable of the three-dimensional image display for the stereoscopic vision, and the CCU 21 generates the two image signals of the image for the right eye and the image for the left eye, and outputs the image signals to the image signal output portion 23. As a result, at the display portion 4, the three-dimensional image is displayed, that is, the image for the right eye and the image for the left eye are alternately displayed, and the user can stereoscopically view the object image by looking at the display portion 4 through the spectacles for the stereoscopic vision including shutters that are alternately opened and closed corresponding to the left and right images for example.

Figure 2:
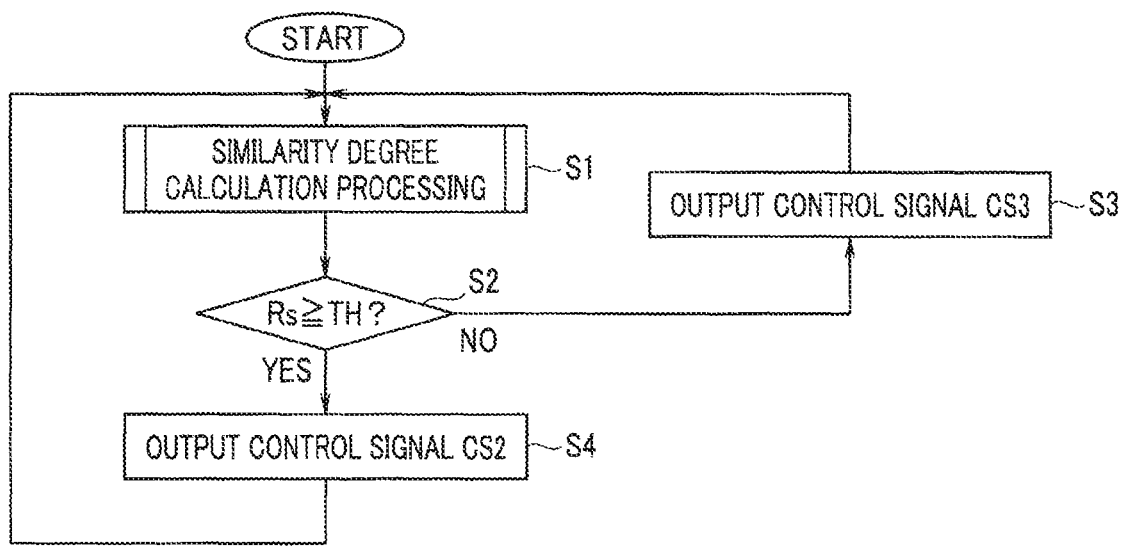
FIG. 2 is a flowchart illustrating an example of a flow of processing of a similarity degree determination portion 22 relating to the embodiment of the present invention.

FIG. 2 is a flowchart illustrating an example of a flow of the processing of the similarity degree determination portion 22.

To the similarity degree determination portion 22, the two image signals of the image for the right eye and the image for the left eye from the CCU 21 are inputted as illustrated in FIG. 1.

The similarity degree determination portion 22 executes similarity degree calculation processing of executing the processing of calculating a similarity degree R of the two image signals of the image for the right eye and the image for the left eye from the CCU 21 in a predetermined period PD (S1).

Figure 3:
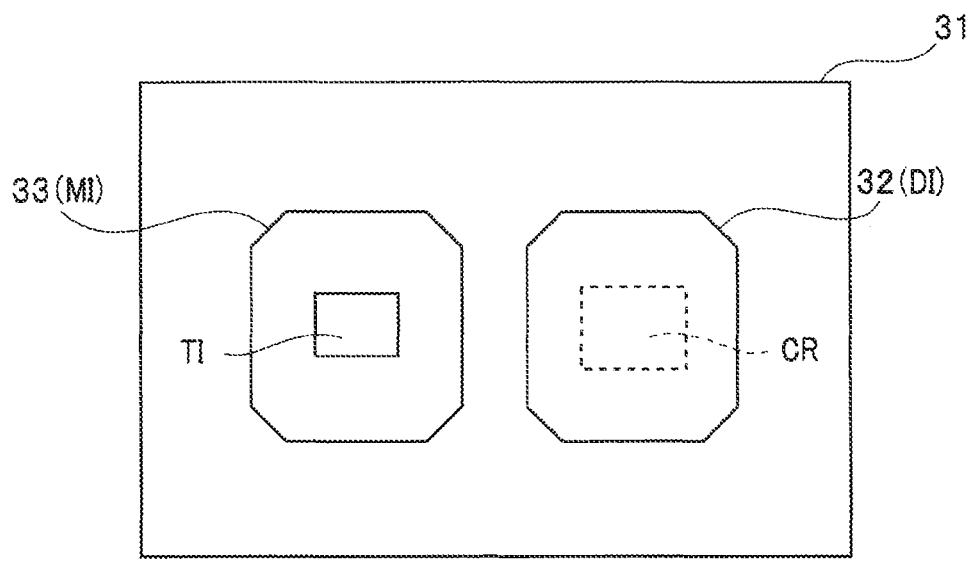
FIG. 3 is a diagram illustrating an example of regions of two images generated in an image pickup device 13, for describing a method of calculating a similarity degree R by a template matching method relating to the embodiment of the present invention.

Here, a calculation method of the similarity degree R will be described. The similarity degree R is calculated as follows. FIG. 3 is a diagram illustrating an example of regions of the two images generated in the image pickup device 13, for describing a method of calculating the similarity degree R by a template matching method.

As illustrated in FIG. 3, an image 31 corresponding to an image pickup surface region of the image pickup device 13 includes two image regions that are an image region for the right eye corresponding to an image 32 for the right eye and an image region for the left eye corresponding to an image 33 for the left eye.

Of the image 32 for the right eye and the image 33 for the left eye, the image (the image 33 for the left eye for example) that is set beforehand is defined as the main image MI, and a partial image of a predetermined region in the main image MI is segmented and defined as the template image TI.

Then, the similarity degree R of the two images is calculated by template matching processing of obtaining whether or not an image exists that coincides with the template image TI, in an entire subordinate image DI (the image for the right eye for example) that is not the main image MI of the image 32 for the right eye and the image 33 for the left eye or in an image CR (indicated by dotted lines) of a region set in the subordinate image DI.

Specifically, in the template matching processing, the template image TI is defined as a rectangular image of M×N (M and N are integers) formed of M pixels and N pixels, and the similarity degree at each position is calculated while moving the template image TI to the subordinate image DI or the image CR in a predetermined order, depending on whether or not the image region exists that coincides with the template image TI in the subordinate image DI or in the image CR superimposed with the template image TI.

When a pixel value at a position (i, j) on the template image TI is defined as T(i, j), and a pixel value at the position (i, j) on the image in the subordinate image DI or the image CR superimposed with the template image TI is defined as I(i, j), the similarity degree R is expressed by a following equation.

(Equation 1)

$$R = \sum_{j=0}^{N-1} \sum_{i=0}^{M-1} (I(i, j) - T(i, j))^2 \quad (1)$$

The equation (1) indicates that a value which is a total sum within M×N pixels of squares of differences of both pixel values is the similarity degree R.

When the template image TI and the image in the subordinate image superimposed with the template image TI completely coincide, R becomes 0 (zero), and as R is closer to 0, a coincidence degree is high, that is, the similarity degree is high.

The similarity degree determination portion 22 executes the template matching processing in the predetermined period PD, and obtains a similarity degree Rs at a position where the similarity degree of the template image TI and the image in the subordinate image DI is highest.

The similarity degree determination portion 22 compares the set threshold TH and the similarity degree Rs, and when the similarity degree Rs is equal to or higher than the threshold TH, outputs the control signal CS2 to output the two-dimensional image to the image signal output portion 23 so as to cause the display portion 4 display the two-dimensional image.

As described above, the similarity degree determination portion 22 that is the similarity degree calculation portion calculates the similarity degree Rs by comparing the image of the region set in the first image of the two images and the image of the region set in the second image of the two images. Here, the similarity degree determination portion 22 calculates the similarity degree Rs by comparing the first image and the second image by the template matching method. The image signal output portion 23 switches from the three-dimensional image signal to the two-dimensional image signal and outputs the two-dimensional image signal to the display portion 4 in a case where the similarity degree is lower than the predetermined threshold TH.

Note that the similarity degree Rs may be calculated using a template matching method other than the template matching method using the above-described equation (1).

Furthermore, the similarity degree Rs may be calculated using a similarity degree determination method other than the template matching method.

For example, each of the image 32 for the right eye and the image 33 for the left eye may be divided into a plurality of regions, and the similarity degree may be calculated based on a brightness distribution of a divided region.

Figure 4:
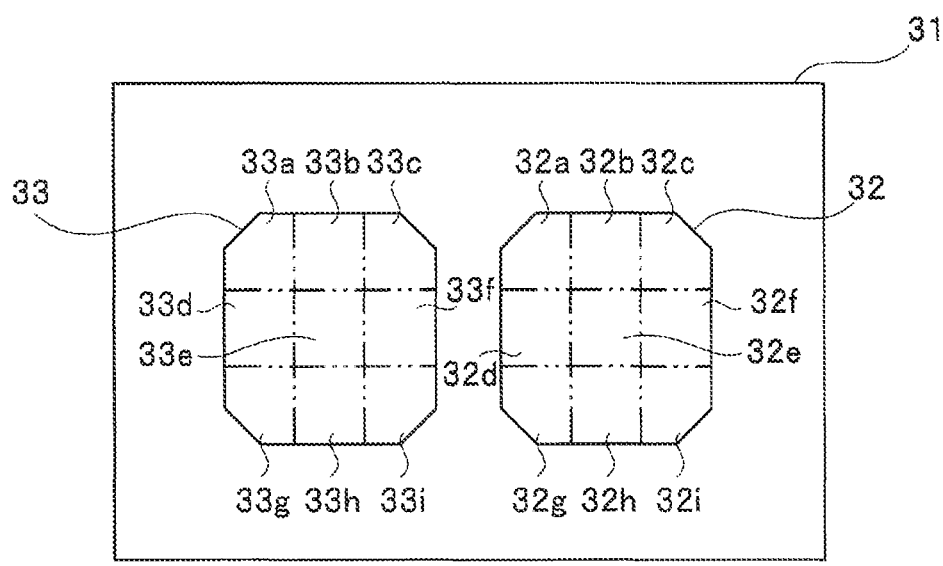
FIG. 4 is a diagram illustrating an example of an image for which each of an image for a right eye and an image for a left eye included in an image signal outputted from the image pickup device 13 is divided, relating to the embodiment of the present invention.

FIG. 4 is a diagram illustrating an example of the image for which each of the image for the right eye and the image for the left eye included in the image signal outputted from the image pickup device 13 is divided.

FIG. 4 illustrates the image 31 obtained by picking up the image by the image pickup device 13. The image 31 outputted from the CCU 21 includes the image 32 for the right eye and the image 33 for the left eye. The image 32 or the right eye and the image 33 for the left eye have the same size and shape.

The similarity degree determination portion 22 extracts the plurality of images for which the image 32 for the right eye is divided in a predetermined shape, and extracts the plurality of images for which the image 33 for the left eye is also divided similarly to the image 32 for the right eye. In FIG. 4, each of the image 32 for the right eye and the image 33 for the left eye is divided into nine image regions.

The divided regions of the image 32 for the right eye and the image 33 for the left eye are set from the condition setting portion 5. That is, a number or a range of the plurality of regions of each of the image 32 for the right eye and the image 33 for the left eye can be set and changed.

The image 32 for the right eye is divided into nine image regions 32$a$-32$i$, and the image 33 for the left eye is divided into nine regions 33$a$-33$i$. The image regions 32$a$-32$i$ of the right eye correspond to the regions 33$a$-33$i$ of the left eye, respectively.

Note that, here, each of the image 32 for the right eye and the image 33 for the left eye is divided into nine image regions; however, each may be divided into a larger number or a smaller number.

The similarity degree determination portion 22 calculates brightness of the respective divided regions 32$a$-32$i$ of the image 32 for the right eye and brightness of the respective divided regions 33$a$-33$i$ of the image 33 for the left eye, compares a brightness distribution of the image 32 for the right eye and the brightness distribution of the image 33 for the left eye, and determines whether or not the distributions are similar.

The brightness of each region is determined from the total sum or an average value of the pixel values of a plurality of pixels in each image.

The similarity degree determination portion 22 calculates a difference in the brightness between the two corresponding divided regions, and when the total sum of the differences is smaller than a predetermined value, it is determined that the image 32 for the right eye and the image 33 for the left eye are similar.

For example, brightness Ra of a region 32$a$ and brightness La of a region 33$a$ are calculated, and a difference (Ra−La) of the brightness is obtained. Similarly, brightness Rb of a region 32$b$ and brightness Lb of a region 33$b$ are calculated, and a difference (Rb−Lb) of the brightness is obtained. The difference is obtained similarly for other regions 32$c$-32$i$ and 32$c$-32$i$. A sum ((Ra−La)+(Rb−Lb)+(Rc−Lc)+(Rd−Ld)+(Re−Le)+(Rf−Lf)+(Rg−La)+(Rh−Lh)+(Ri−Li)) of the obtained nine difference values is defined as the similarity degree R, and when the similarity degree R is lower than the predetermined value, it is determined that the image 32 for the right eye and the image 33 for the left eye are similar.

If a foreign matter is stuck to one observation window, since the similarity degree Rs which is the total sum of the difference values becomes equal to or higher than the predetermined value, it is determined that the image 32 for the right eye and the image 33 for the left eye are not similar.

The similarity degree determination portion 22 outputs the control signal CS2 to cause the two-dimensional image to be outputted to the image signal output portion 23 when the similarity degree Rs which is the total sum of the difference values of the brightness is equal to or higher than the predetermined value and it is determined that the image 32 for the right eye and the image 33 for the left eye are not similar, and outputs the control signal CS3 to cause the three-dimensional image to be outputted to the image signal output portion 23 when the similarity degree Rs which is the total sum of the difference values of the brightness is lower than the predetermined value and it is determined that the image 32 for the right eye and the image 33 for the left eye are similar.

As described above, the similarity degree determination portion 22 calculates the similarity degree Rs by comparing the brightness distribution of the image 32 for the right eye and the brightness distribution of the image 33 for the left eye. Specifically, the image 32 for the right eye is divided into the plurality of regions, and the image 33 for the left eye is also divided into the plurality similarly to the image 32 for the right eye. Then, the similarity degree determination portion 22 calculates the similarity degree Rs by comparing the brightness distribution of the plurality of divided regions of the image 32 for the right eye as the brightness distribution of the image 32 for the right eye and the brightness distribution of the plurality of divided regions of the image 33 for the left eye as the brightness distribution of the image 33 for the left eye.

Therefore, the similarity degree of the two images can be determined also based on such a brightness distribution in the image.

Note that the sum of the difference values may be calculated by weighting the respective regions. For example, to regions 32$e$ and 33$e$ at center portions of the respective images that are the image 32 for the right eye and the image 33 for the left eye, weighting higher than the weighting to the respective surrounding regions 32$a$ and 32$b$ and the like and 33$a$ and 33$b$ and the like may be performed.

For example, the weighting is performed such that highest weighting is performed for the regions at the center portions of the respective images that are the image 32 for the right eye and the image 33 for the left eye from the plurality of divided regions, and the weighting is gradually lowered toward peripheral regions.

That is, the weighting for the calculation of the similarity degree is performed to each of the plurality of regions, and the similarity degree determination portion 22 calculates the similarity degree by comparing the brightness distribution of the image 32 for the right eye and the image 33 for the left eye for which the weighting is performed to the respective regions.

In addition, by turning a weighting coefficient to 0 (zero), a desired divided region can be excluded from a target of the calculation of the similarity degree R. By turning the weighting coefficient to 0 (zero), a region not to be the target of the calculation of the similarity degree can be set in the plurality of divided regions.

The weighting coefficient or an excluded region is set or specified from the condition setting portion 5 by the user for example.

Further, the similarity degree R of the image 32 for the right eye and the image 33 for the left eye may be calculated by methods other than template matching determination and brightness distribution determination.

Returning to FIG. 2, the similarity degree determination portion 22 determines whether or not the calculated similarity degree Rs is equal to or higher than the predetermined threshold TH (S2).

When the calculated similarity degree Rs is lower than the predetermined threshold TH (S2: NO), the similarity degree determination portion 22 outputs the control signal CS3 to cause the three-dimensional image to be outputted to the image signal output portion 23 (S3), and returns to the processing of S1.

When the calculated similarity degree Rs is equal to or higher than the predetermined threshold TH (S2: YES), the similarity degree determination portion 22 outputs the control signal CS2 to cause the two-dimensional image to be outputted to the image signal output portion 23 (S4), and returns to the processing of S1.

The similarity degree determination portion 22 repeats the processing of S1-S4.

By the processing in FIG. 2 being executed, when a foreign matter such as liquid is stuck to the observation window and the value of the similarity degree Rs becomes high and becomes equal to or higher than the threshold TH while the three-dimensional image is displayed at the display portion 4, the similarity degree determination portion 22 outputs the control signal CS2 to output the two-dimensional image to the image signal output portion 23. The similarity degree determination portion 22 calculates the similarity degree Rs and compares the similarity degree Rs with the threshold TH in every predetermined period PD, and when the value of the calculated similarity degree Rs is equal to or higher than the predetermined threshold TH, outputs the control signal CS2 to cause the two-dimensional image to be outputted to the image signal output portion 23 at all times.

When receiving the control signal CS2 to output the two-dimensional image from the similarity degree determination portion 22, the image signal output portion 23 outputs only one of the image for the right eye and the image for the left eye.

Note that the image signal output portion 23 may output either image of the image for the right eye and the image for the left eye, but outputs the image of higher contrast between the image for the right eye and the image for the left eye. The image of the higher contrast is the image generated based on light which has passed through the observation window where the foreign matter is not stuck or an amount of the stuck foreign matter is small. Therefore, the image signal output portion 23 also performs the processing of obtaining the contrast of the image 32 for the right eye and the image 33 for the left eye that are inputted.

That is, the image signal output portion 23 outputs the image signal of the image of the higher contrast between the image for the right eye and the image for the left eye, as the two-dimensional image signal formed of either one of the image signal for the image for the right eye and the image signal of the image for the left eye.

The processing in FIG. 2 is executed at all times, and even while the two-dimensional image is displayed at the display portion 4, image comparison processing described above is performed in a background in the predetermined period PD. Therefore, when the foreign matter is removed by air/water feeding or flows down and disappears from the observation window and the value of the similarity degree R becomes low and becomes lower than the threshold TH while the two-dimensional image is displayed at the display portion 4, the similarity degree determination portion 22 does not output the control signal CS2 to cause the two-dimensional image to be outputted to the image signal output portion 23.

When the similarity degree determination portion 22 stops outputting the control signal CS2 to cause the two-dimensional image to be outputted to the image signal output portion 23, the image signal output portion 23 outputs both of the image 32 for the right eye and the image 33 for the left eye for displaying the three-dimensional image to the display portion 4.

Figure 5:
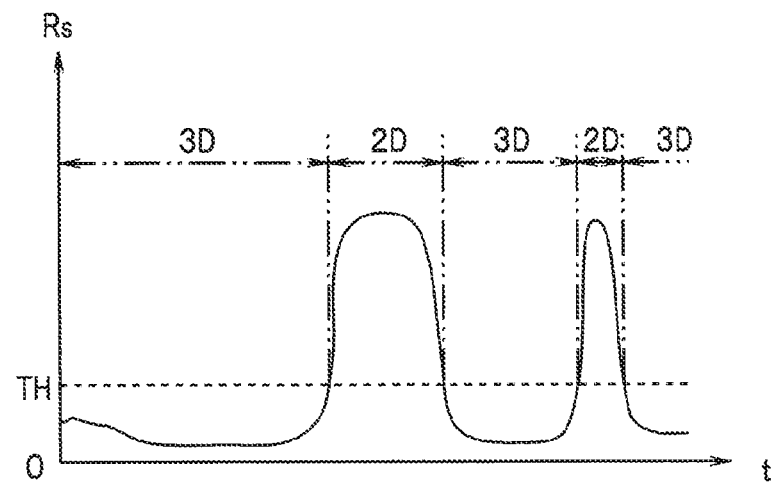
FIG. 5 is a diagram illustrating a switching state of an image displayed at a display portion 4, with a lapse of time, relating to the embodiment of the present invention.

FIG. 5 is a diagram illustrating a switching state of the image displayed at the display portion 4 with a lapse of time. A horizontal axis in FIG. 5 is time t, and a vertical axis corresponds to the similarity degree R.

FIG. 5 illustrates that the similarity degree Rs calculated in the similarity degree determination portion 22 changes with the lapse of time, the two-dimensional image (2D) is displayed when the similarity degree Rs becomes equal to or higher than the predetermined threshold TH, and the three-dimensional image (3D) is displayed when the similarity degree Rs is lower than the predetermined threshold TH.

As described above, according to the above-described embodiment, the stereoscopic endoscope apparatus capable of correctly switching the display of the two-dimensional image and the three-dimensional image can be provided.

For example, in a medical field, the endoscope 2 is sometimes used by inserting the insertion portion 2a into a lumen of a digestive organ or the like, and on a distal end portion of the insertion portion 2a of the endoscope 2, an air/water feeding nozzle is provided so as to remove the foreign matter stuck to the observation window.

A lot of residues or the like exist inside digestive organs or the like, and the foreign matter is easily stuck to the observation window. When it is recognized that the foreign matter is stuck to the observation window from an endoscopic image displayed at the display portion 4, the operator who is the user can remove the foreign matter stuck to the observation window by jetting of water and air by depressing an air/water feeding button provided in an operation portion and perform a switching operation to the two-dimensional image display; however, it is troublesome for the user.

However, according to the endoscope apparatus described above, in the case where the foreign matter is stuck only to the two observation windows for the stereoscopic vision, since the three-dimensional image is automatically switched to the two-dimensional image, the user can continuously perform observation or the like without troublesome button operations.

Next, modifications will be described.

Modification 1

While the stereoscopic endoscope apparatus of the embodiment described above is configured such that the light made incident on the two observation windows 11R and 11L forms the image on the image pickup surface of one image pickup device 13, the light made incident on the observation windows 11R and 11L may be made incident on different image pickup devices respectively.

Figure 6:
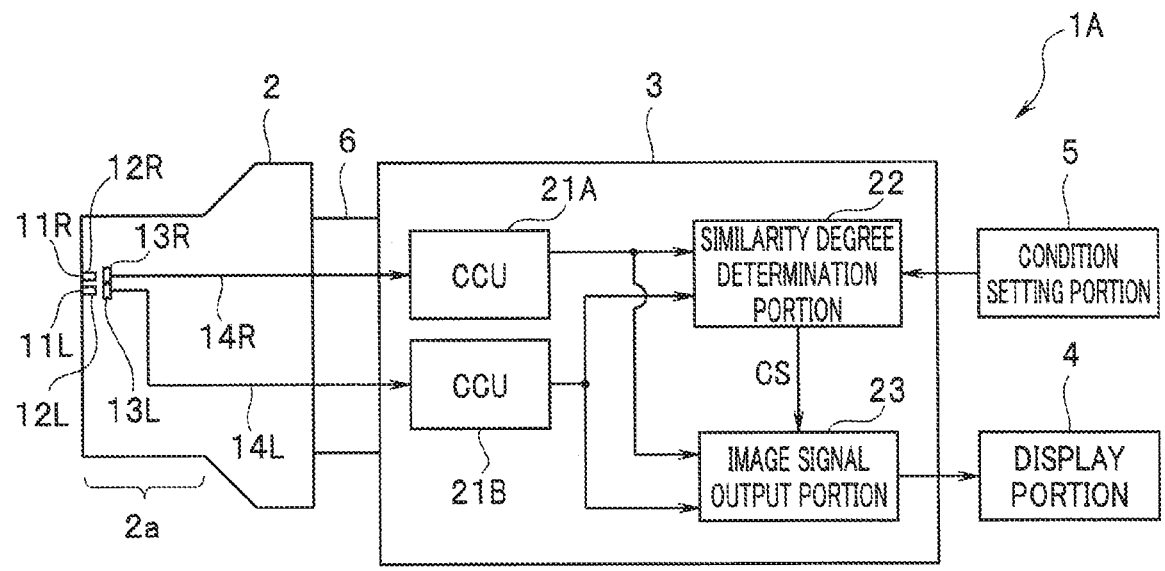
FIG. 6 is a configuration diagram illustrating a configuration of the stereoscopic endoscope apparatus relating to a modification 1 of the embodiment of the present invention.

FIG. 6 is a configuration diagram illustrating the configuration of the stereoscopic endoscope apparatus relating to the modification 1 of the present embodiment. In FIG. 6, the same signs are attached to components the same as the components in FIG. 1 and description will be omitted.

A stereoscopic endoscope apparatus 1A relating to the modification illustrated in FIG. 6 is configured to make the light made incident on the two observation windows 11R and 11L be incident on image pickup devices 13R and 13L respectively. Then, the two image pickup devices 13R and 13L output the image signals for the right eye and for the left eye to CCUs 21R and 21L respectively.

That is, the image pickup devices 13R and 13L configure the image pickup portion configured to pick up the optical images for the right eye and for the left eye formed by the objective optical systems 12R and 12L that form the left and right optical images.

From the two CCUs 21R and 21L, the image for the right eye and the image for the left eye are respectively outputted to the similarity degree determination portion 22 and the image signal output portion 23. Operations of the similarity degree determination portion 22 and the image signal output portion 23 are the same as the operations described in the above-described embodiment.

The stereoscopic endoscope apparatus 1A relating to the present modification also have effects similar to the effects of the stereoscopic endoscope apparatus 1 of the above-described embodiment.

Modification 2

In the above-described embodiment, the similarity degree determination portion 22 outputs the control signal CS2 to cause the two-dimensional image to be outputted to the image signal output portion 23 when the similarity degree R becomes equal to or higher than the predetermined threshold TH, and the image signal output portion 23 outputs only one (the image of the higher contrast for example) of the image for the right eye and the image for the left eye to the display portion 4 so as to display the two-dimensional image at the display portion 4 when receiving the control signal CS2 to cause the two-dimensional image to be outputted.

In contrast, in the modification 1, the stereoscopic endoscope is configured so as not to display the two-dimensional image at the display portion 4 when a state where the similarity degree R is equal to or higher than the predetermined threshold TH does not continue for a predetermined time period or longer.

For example, in the above-described embodiment, even when the foreign matter is stuck to the observation window only for a short time period, the similarity degree Rs becomes the value equal to or higher than the predetermined threshold TH, and sometimes the display is immediately changed to the two-dimensional image. Thereafter, when the foreign matter disappears from the observation window and the similarity degree Rs becomes the value lower than the predetermined threshold TH, the display returns to the three-dimensional image. When the three-dimensional image and the two-dimensional image are switched frequently in this way, the image displayed at the display portion 4 becomes the image that is difficult to see for the user.

Therefore, in the present modification 2, in order to prevent such switching of the image in a short time period, the similarity degree determination portion 22 outputs the control signal CS2 to cause the two-dimensional image to be outputted to the image signal output portion 23, when the similarity degree Rs is equal to or higher than the predetermined threshold TH for a predetermined time period TT or longer. Note that the predetermined time period TT can be set and changed from the condition setting portion 5.

Figure 7:
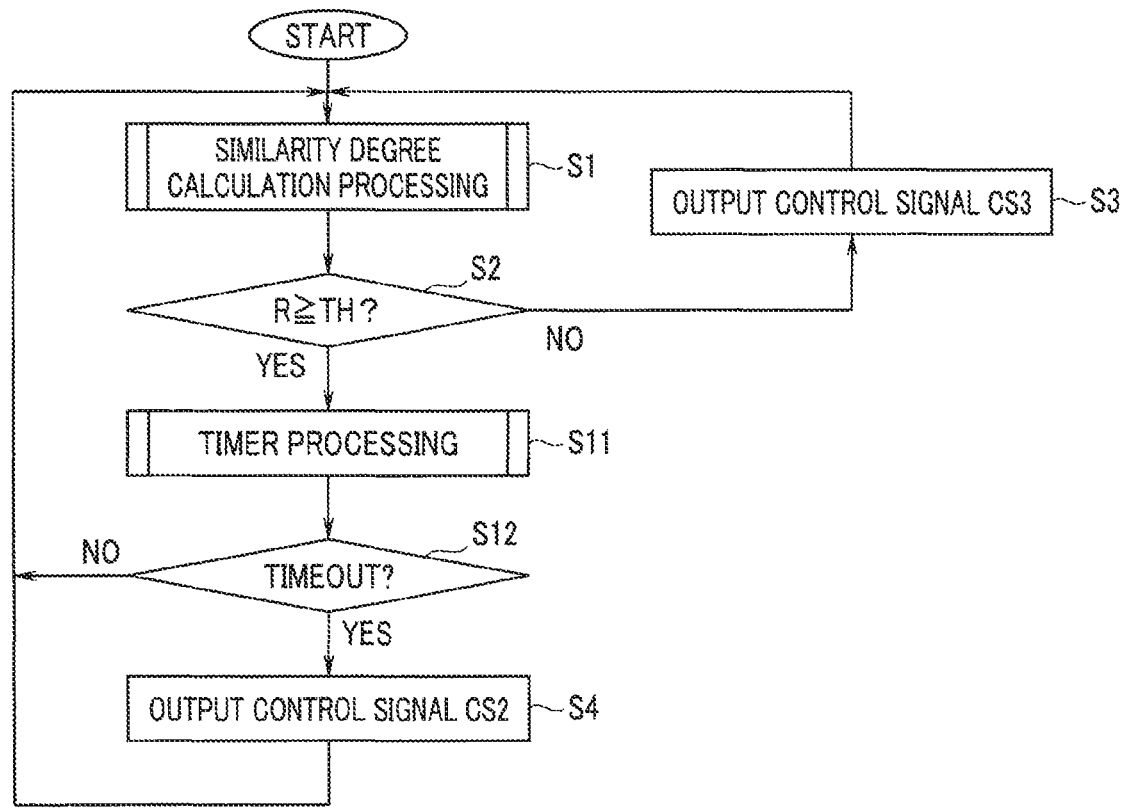
FIG. 7 is a flowchart illustrating an example of the flow of the processing of the similarity degree determination portion 22 relating to a modification 2 of the embodiment of the present invention.

FIG. 7 is a flowchart illustrating an example of the flow of the processing of the similarity degree determination portion 22 relating to the present modification 2.

In FIG. 7, the same step numbers are attached for the processing the same as the processing in FIG. 2, and the description is simplified.

While the similarity degree determination portion 22 executes the similarity degree calculation processing (S1) and the comparison processing (S2), when the calculated similarity degree Rs is lower than the predetermined threshold TH (S2: NO), the similarity degree determination portion 22 executes the processing of S3 and then returns to the processing of S1.

When the calculated similarity degree Rs is equal to or higher than the predetermined threshold TH (S2: YES), the similarity degree determination portion 22 executes timer processing (S11).

In the timer processing of S11, a count by a predetermined timer, a software timer for example, is started when the similarity degree Rs becomes equal to or higher than the predetermined threshold TH. The similarity degree determination portion 22 executes the processing of S1 and S2 in the predetermined period PD, and when it is determined that the similarity degree Rs is equal to or higher than the predetermined threshold TH, it is YES in S2.

In the timer processing of S11, the count is counted up or counted down when it is continuously determined that the similarity degree Rs is equal to or higher than the predetermined threshold TH, and a timer is cleared in the case where the determination that the similarity degree Rs is equal to or higher than the predetermined threshold TH is not continuously generated.

The time period set to the timer is, for example, an average value of general air/water feeding time period for washing the observation window. When a count value according to the average time period of the air/water feeding is set, the three-dimensional image is not switched to the two-dimensional image even when the user performs normal air/water feeding processing so that the user can smoothly perform the observation or the like by the three-dimensional image.

Note that the timer may be cleared while the air/water feeding button is operated so as not to switch to the two-dimensional image while the air/water feeding is being performed.

The similarity degree determination portion 22 determines whether or not it is timeout by the count by the timer processing of S11 (S12). Whether or not it is the timeout is determined, for example, depending on whether the count value which has been counted up from 0 becomes a predetermined count value or depending on whether the count value which has been counted down from the predetermined count value becomes 0 in the timeout timer processing.

When it is not the timeout (S12: NO), the processing returns to S1.

When it is the timeout (S12: YES), the similarity degree determination portion 22 outputs the control signal CS2 to cause the two-dimensional image to be outputted to the image signal output portion 23 (S3).

By the processing in FIG. 7 being executed, when the foreign matter such as liquid is stuck to the observation window, the value of the similarity degree Rs becomes high and becomes equal to or higher than the threshold TH and the state where the value of the similarity degree Rs is equal to or higher than the threshold TH continues for a predetermined time period or longer while the three-dimensional image is displayed at the display portion 4, the similarity degree determination portion 22 outputs the control signal CS2 to output the two-dimensional image to the image signal output portion 23.

Therefore, since the three-dimensional image and the two-dimensional image are not frequently switched, the image displayed at the display portion 4 does not become the image that is difficult to see for the user.

Modification 3

In the above-described embodiment and the above-described respective modifications, the similarity degree determination portion 22 calculates the predetermined similarity degree Rs and compares the similarity degree Rs with the threshold TH; however, a plurality of similarity degrees that are different from each other may be calculated and whether or not the image 32 for the right eye and the image 33 for the left eye are similar may be determined based on the plurality of similarity degrees.

Figure 8:
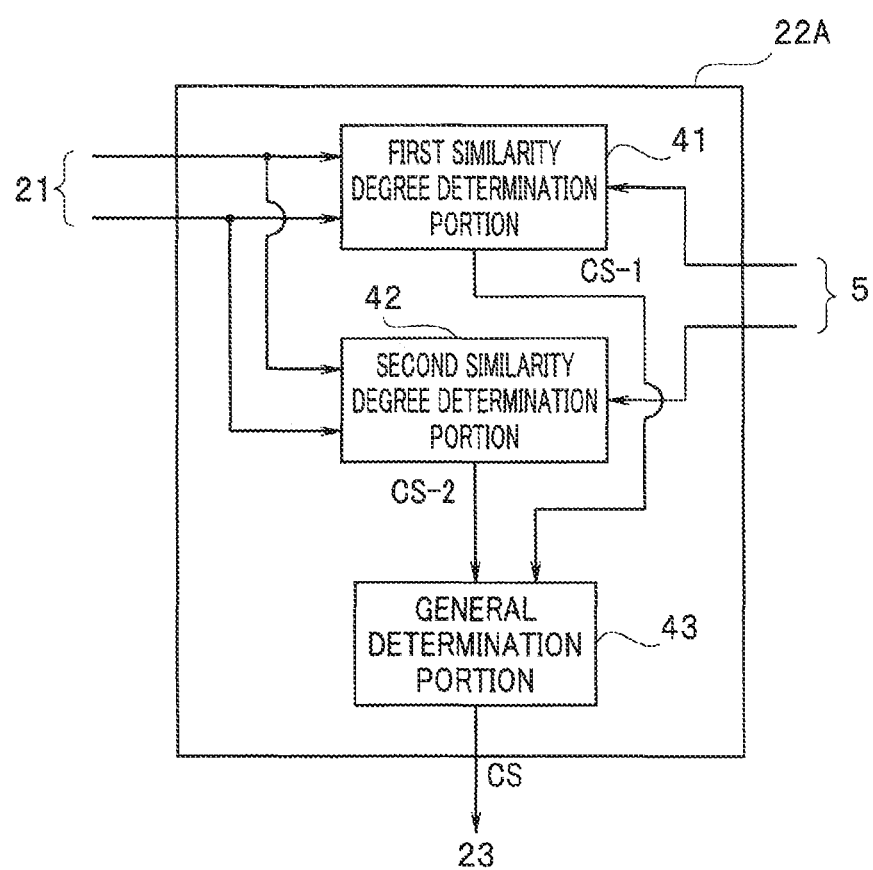
FIG. 8 is a block diagram illustrating a configuration of a similarity degree determination portion 22A relating to a modification 3 of the embodiment of the present invention.

FIG. 8 is a block diagram illustrating the configuration of a similarity degree determination portion 22A relating to the modification 3.

The similarity degree determination portion 22A includes two similarity degree determination portions 41 and 42, and a general determination portion 43. A first similarity degree determination portion 41 is, for example, a processing portion configured to calculate a similarity degree Rs1 by the pattern matching processing described above, and a second similarity degree determination portion 42 is a processing portion configured to calculate a similarity degree Rs2 by the brightness distribution of the divided regions divided into the plurality of regions described above.

To the respective similarity degree determination portions 41 and 42, the two image signals of the image for the right eye and the image for the left eye from the CCU 21 are inputted.

The condition setting portion 5 is connected to the respective similarity degree determination portions 41 and 42, and can input and set various kinds of conditions.

The general determination portion 43 finally determines whether the image 32 for the right eye and the image 33 for the left eye are similar based on two determination signals CS-1 and CS-2 outputted from the two similarity degree determination portions 41 and 42, and supplies the determination signal CS to the image signal output portion 23.

For example, the general determination portion 43 can make a determination that the general determination portion 43 outputs the control signal CS2 to output the two-dimensional image to the image signal output portion 23 only when the two determination signals CS-1 and CS-2 both determine that the image for the right eye and the image for the left eye are similar (the similarity degree is lower than the threshold for example), or the general determination portion 43 outputs the control signal CS2 to output the two-dimensional image to the image signal output portion 23 only when the determination signal CS-1 determines that the image for the right eye and the image for the left eye are similar and then the determination signal CS-2 determines that the image for the right eye and the image for the left eye are similar, or the like.

That is, the similarity degree determination portion 22 calculates the plurality of similarity degrees by the different methods, and the image signal output portion 23 switches and outputs the three-dimensional image signal and the two-dimensional image signal based on the plurality of calculated similarity degrees.

According to such a configuration, whether the image 32 for the right eye and the image 33 for the left eye are similar can be more surely determined.

In the above-described example, the two similarity degree determination portions 41 and 42 are used to determine the similarity degree of the image by the template matching processing and to determine the similarity degree of the image by the brightness distribution determination of the divided regions respectively; however, the number of similarity degree determination portions may be three or more, and the similarity degree may be determined by other methods for the similarity degree determination.

As described above, according to the embodiment and the respective modifications described above, the stereoscopic endoscope apparatus capable of correctly switching the display of the two-dimensional image and the three-dimensional image can be provided.

Note that, in the embodiment and the respective modifications, when displaying the image for the two-dimensional display, the signal of the image for the two-dimensional display to be the image for the right eye and the image for the left eye is generated from the images acquired by the observation windows 11R and 11L and is outputted to the display portion 4; however, the signal of the image acquired by either one of the observation windows 11R and 11L may be directly transmitted to the display portion 4 and displayed without generating the signal of the image for the right eye and the image for the left eye.

According to the configuration, the operator can, for example, simultaneously display the plurality of the images for the two-dimensional display of either for the right eye or for the left eye at the display portion 4 and observe the images in a state of taking off the spectacles for the stereoscopic vision. When switching the display from the image for the two-dimensional display to the image for the three-dimensional display, setting of the display portion 4 is switched so as to display the image for the three-dimensional display, and the operator puts on the spectacles for the stereoscopic vision and observes the image for the three-dimensional display.

The present invention is not limited to the embodiment described above, and various changes and modifications or the like are possible without changing a subject matter of the present invention.

What is claimed is:
1. A stereoscopic endoscope apparatus comprising:
an image pickup sensor configured to pick up first and second optical images formed by an objective optical system configured to form the first and second optical images; and
a processor comprising hardware, the processor being configured to:
receive input of a first image signal based on the first optical image and a second image signal based on the second optical image outputted from the image pickup sensor, compare a first image based on the first image signal and a second image based on the second image signal, and calculate a similarity degree between the first image and the second image; and switch from a three-dimensional image signal formed of the first image signal and the second image signal to a two-dimensional image signal formed of either one of the first and second image signals based on an image with fewer foreign matters between the first image signal and the second image signal and output the two-dimensional image signal, when, due to sticking of the foreign matters to a portion of the objective optical system, the similarity degree becomes lower than the similarity degree when the foreign matters are not stuck to the objective optical system.

2. The stereoscopic endoscope apparatus according to claim 1, wherein the processor switches from the two-dimensional image signal formed of either one of the first image signal and the second image signal to the three-dimensional image signal formed of the first image signal and the second image signal and outputs the three-dimensional image signal, when the foreign matters are removed from the objective optical system and a state where the similarity degree is low becomes a state where the similarity degree is high.

3. The stereoscopic endoscope apparatus according to claim 1,
wherein the image pickup sensor picks up the first optical image for a right eye formed by the objective optical system and the second optical image for a left eye formed by the objective optical system, and
the processor compares the first image and the second image and calculates the similarity degree by receiving input of an image signal for the right eye based on the first optical image and an image signal for the left eye based on the second optical image outputted from the image pickup sensor.

4. The stereoscopic endoscope apparatus according to claim 1, wherein the processor compares an image of a region set in the first image and an image of a region set in the second image, and calculates the similarity degree.

5. The stereoscopic endoscope apparatus according to claim 1, wherein the processor compares the first image and the second image by a template matching method, and calculates the similarity degree.

6. The stereoscopic endoscope apparatus according to claim 1, wherein the processor compares a first brightness distribution of the first image and a second brightness distribution of the second image, and calculates the similarity degree.

7. The stereoscopic endoscope apparatus according to claim 6,
wherein the first image is divided into a plurality of regions, the second image is divided into a plurality of regions similarly to the first image, and
the processor compares a brightness distribution of the plurality of divided regions of the first image as the first brightness distribution and a brightness distribution of the plurality of divided regions of the second image as the second brightness distribution, and calculates the similarity degree.

8. The stereoscopic endoscope apparatus according to claim 7, wherein the processor is configured to receive a condition to change setting regarding a number or a range of the plurality of regions of each of the first image and the second image.

9. The stereoscopic endoscope apparatus according to claim 7, wherein the processor is configured to:
receive a condition to perform weighting for calculation of the similarity degree to each of the plurality of regions, and
compare the first and second brightness distributions to which the weighting is performed for the respective regions and calculate the similarity degree.

10. The stereoscopic endoscope apparatus according to claim 7, wherein the processor is configured to receive a condition to set a region not to be a target of calculation of the similarity degree in the plurality of regions.

11. The stereoscopic endoscope apparatus according to claim 1, wherein the processor is configured to:
calculate a plurality of similarity degrees by different methods, and
switch and output the three-dimensional image signal and the two-dimensional image signal based on the plurality of calculated similarity degrees.

12. The stereoscopic endoscope apparatus according to claim 1, wherein the controller is configured to receive a condition to set a period of switching the three-dimensional image signal and the two-dimensional image signal.

13. The stereoscopic endoscope apparatus according to claim 1, wherein the processor outputs an image signal of an image of higher contrast between the first image and the second image, as the two-dimensional image signal formed of either one of the first image signal and the second image signal.

14. A processor configured to:
receive a first image signal generated by image pickup of a first optical image formed by an objective optical system and a second image signal generated by image pickup of a second optical image formed by the objective optical system, compare a first image based on the first image signal and a second image based on the second image signal, and calculate a similarity degree between the first image and the second image; and
switch from a three-dimensional image signal formed of the first image signal and the second image signal to a two-dimensional image signal formed of either one of the first and second image signals based on an image with fewer foreign matters between the first image signal and the second image signal and output the two-dimensional image signal, when, due to sticking of the foreign matters to a portion of the objective optical system, the similarity degree becomes lower than the similarity degree when the foreign matters are not stuck to the objective optical system.

* * * * *